US006926889B2

(12) United States Patent
Husseneder et al.

(10) Patent No.: US 6,926,889 B2
(45) Date of Patent: Aug. 9, 2005

(54) RECOMBINANT BACTERIA FOR USE IN INSECT CONTROL

(75) Inventors: Claudia Husseneder, Honolulu, HI (US); J. Kenneth Grace, Kaneohe, HI (US); Darcy E. Oishi, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 163 days.

(21) Appl. No.: 10/062,821

(22) Filed: Feb. 1, 2002

(65) Prior Publication Data

US 2002/0119556 A1 Aug. 29, 2002

Related U.S. Application Data

(60) Provisional application No. 60/266,895, filed on Feb. 2, 2001.

(51) Int. Cl.[7] .......................... A01N 63/00; C12N 1/21; C12N 15/74
(52) U.S. Cl. .................. 424/93.2; 424/93.4; 424/93.48; 424/405; 435/252.3; 435/471
(58) Field of Search ............................. 424/93.2, 405, 424/93.48, 93.4; 435/252.3, 471; 800/21

(56) References Cited

FOREIGN PATENT DOCUMENTS

WO WO 9402591 A1 * 2/1994

OTHER PUBLICATIONS

Watanabe et al., "Biological control of an insect pest by gut colonizing Enterobacter clacoe transformed with ice nucleation gene," J. Appl. Microbiol. 88(1): 90–97, Jan. 2000.*

Thanabalu et al., "Expression of the mosquitocidal toxins of Bacillus sphaericus and Bacillus thuringensis subsp. israelensis by recombinant Caulobacter crescentus. . .", Appl. Environ. Microbiol. 58(3): 905–910, Mar. 1992.*

Liu et al., "Efficient synthesis of mosquitocidal toxins in Asticcacaulis excentricus demonstrates potential of gram–negative bacteria in mosquito control," Nat. Biotech. 14(3): 343–347, Mar. 1996.*

Khampang et al., "Efficient expression of mosquito–larvicidal proteins in a gram–negative bacterium cpable of recolonization in the guts of Anopheles dirus larvae," (Appl. Microbiol. Biotechnol. 51: 79–84, 1999).*

McKillip et al. "Sporogenous midgut bacteria of the leafroller, Pandemis pyrusana (Lepidoptera: Tortricidae)," Environ. Entomol. 26 (6): 1475–1481, Dec. 1997.*

* cited by examiner

*Primary Examiner*—Scott D. Priebe
(74) *Attorney, Agent, or Firm*—Nixon Peabody LLP

(57) ABSTRACT

The present invention relates to recombinant bacteria genetically engineered from insect hosts to express toxic gene products in a pest insect. The present invention also relates to a method of controlling an insect population using such a recombinant bacteria as a delivery agent throughout an insect colony. The invention also relates to a method of delivering and expressing a gene in an insect.

16 Claims, 7 Drawing Sheets

RECOMBINANT BACTERIA FOR USE IN INSECT CONTROL

Figure 1:
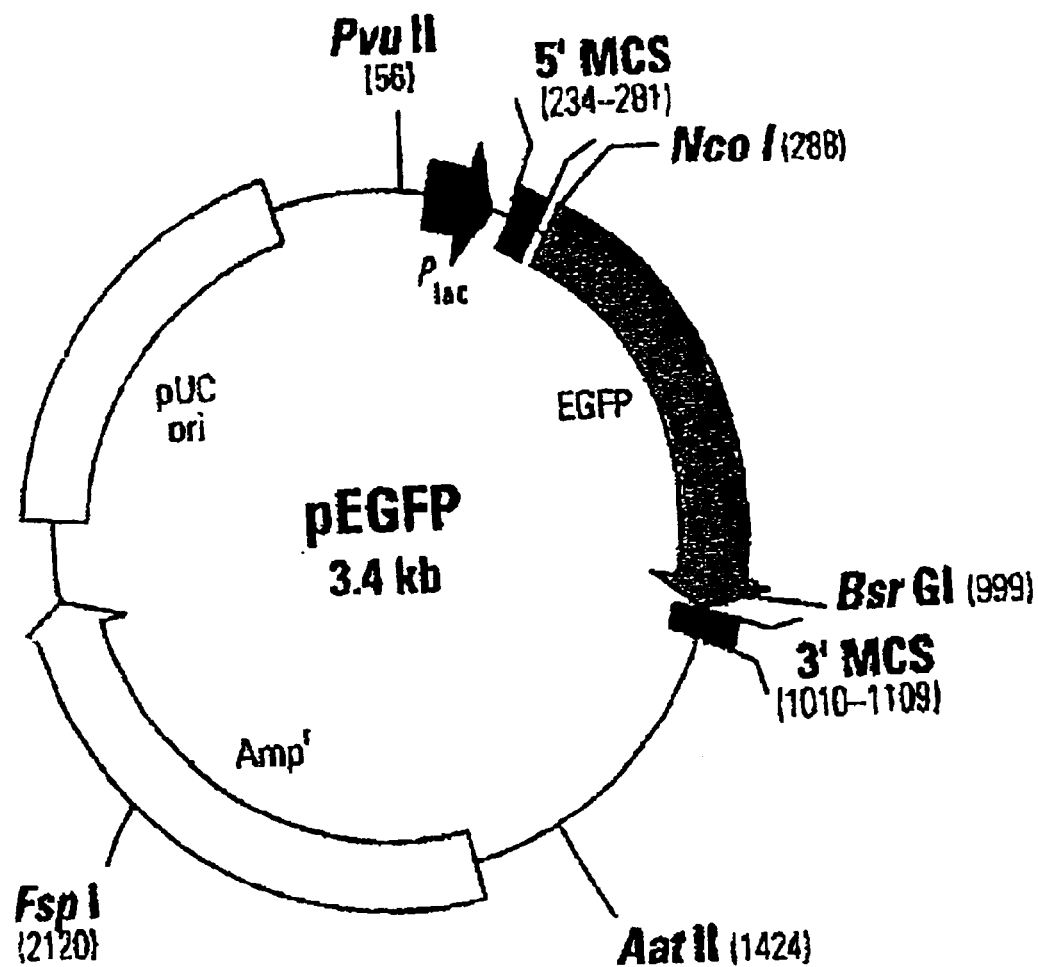

The present invention claims benefit of U.S. Provisional Patent Application Ser. No. 60/266,895 filed Feb. 2, 2001.

The subject matter of this application was made with support from the United States Government under USDA-ARS Contract No. 58-6435-8-107 (Account No. 655861). The U.S. Government may have certain rights.

FIELD OF THE INVENTION

The present invention relates to genetically modified bacteria derived from insect hosts and the use of such modified bacteria as a shuttle system to deliver and express genes for the control of insect pests.

BACKGROUND OF THE INVENTION

Many of the ecologically and economically important insect pests are social or subsocial, such as termites, ants and cockroaches. They live in groups and colonies and engage in social interactions, such as mutual grooming and food sharing. Reproduction in a social insect colony is the responsibility of specialized individuals, the reproductives. To eliminate an entire colony, it is necessary to kill not only the foraging population but also the reproductives. An insect colony can occupy a very large area and have a considerable number of foragers (millions), and the location of the nest containing the reproductives is usually difficult to pinpoint, particularly in the case of subterranean termites and ants. Therefore, control of social insects by eliminating entire colonies is challenging. Control of such pests is of economic significance throughout the world. In the United States, for example, the cost of damage and control due to the Formosan subterranean termite (*Coptotermes formosanus* Shiraki, Isoptera: Rhinotermitidae), a serious invasive pest species found in southeast United States and Hawaii, is estimated at $1 billion annually.

Chemical control methods are associated with certain risks and shortcomings. After the ban of certain soil insecticides (chlordane and other cyclodienes), public demand for reduced-risk, environmentally friendly techniques for pest control has increased. One of the most promising reduced-risk approaches to social insect control that has recently emerged is the targeted bait approach using slow-acting toxicants, such as insect growth regulators (Su et al., "A Review of Subterranean Termite Control Practices and Prospects for Integrated Pest Management Programmes," *Integr. Pest. Management Rev.* 3:1–13 (1998)). In baiting stations, foragers consume the bait toxicant. Suppression of a colony depends on the transmission of the active ingredient through the colony via food exchange and grooming among nest mates. A limitation of current baiting schemes is that a large number of foragers must directly contact the bait to spread it throughout a colony. This is because the concentration of bait toxicant is diluted as it is passed from one individual to another during social interactions, until such small amounts are passed that they are not effective against the recipient.

Theoretically, baiting systems could be improved by employing self-sustaining, self-replicating and self-perpetuating biological control agents, such as nematodes, viruses, fungi, and bacteria. Although there is evidence that some of these entomopathogens have effects on insects in lab studies, they have failed to meet expectations in field trials (Culliney et al., "Prospects of the Biological Control of Subterranean Termites (Isoptera: Rhinotermitidae), with Special Reference to *Coptotermes formosanus*." *Bull. Ent. Res.* 90:9–21 (2000)). Their successful use as biocontrol agents is limited due to biological constraints and logistical problems when dealing with social insects. For example, the potency of most pathogens is too weak in their natural state, and they are not generally persistent in the environment. In addition, the target insects are able to recognize and avoid contact with pathogens (Grace, J. K, "Microbial Termite Control," in *Hawaii Agriculture: Positioning for Growth*," CTAHR Proceedings, University of Hawaii, pp. 166–167 (1995)), remove them from their nestmates through grooming behavior, and isolate infected individuals from the colony (Lai, P.Y., "Biology and Ecology of the Formosan Subterranean Termite, *Coptotermes formosanus*, and Its Susceptibility to the Entomogenous Fungi, *Beauveria bassiana and Metarrhizium* [sic] *anisopliae*," Ph. D. Diss., University of Hawaii, 140 pp. (1977)). Insects also have an efficient immune system for dealing with infections of foreign pathogenic microbes. Therefore, delivery of the pathogen throughout an entire colony would require a large number of initially inoculated individuals and a high dose of inoculum, just as with a chemical bait. This is difficult to achieve when dealing with insects that are not easily accessible, such as ants and termites that live in the soil. Thus, with these foreign pathogens, the level of mass production and re-applications that are required to affect insect groups is expensive, time and labor intensive, not justified by the poor performance, limited to the immediate area of application, and has only a temporary effect (Culliney et al., "Prospects of the Biological Control of Subterranean Termites (Isoptera: Rhinotermitidae), with Special Reference to *Coptotermes formosanus*." *Bull. Ent. Res.* 90:9–21 (2000); and Grace, J. K., "Biological Control Strategies for Suppression of Termites," *J. Agric. Entomol.* 14:281–289 (1997)).

The present invention is directed to overcoming these and other deficiencies in the art.

SUMMARY OF THE INVENTION

The present invention relates to a bacterium for the control of insects. The bacterium, which is endogenous to the insect to be controlled, is transformed with a nucleic acid construct having a nucleic acid molecule that is exogenous (i.e, foreign) to the bacterium, and encodes a protein or polypeptide that is toxic to insects. The exogenous nucleic acid molecule is operatively linked to transcriptional and translational control elements for expression of that nucleic acid in the insect.

The present invention also relates to a method for insect control. This method involves isolating a bacterium that is endogenous to the insect to be controlled. The bacterium is transformed with a nucleic acid molecule encoding a protein or polypeptide which, when expressed in the insect, is toxic to the insect. The transformed bacterium is then introduced into the food source of the insect to be controlled.

The present invention also relates to a method of delivering and expressing a gene in an insect. This method involves isolating a bacterium endogenous to the insect and transforming that bacterium with a nucleic acid molecule encoding a protein or polypeptide which is exogenous (i.e., foreign) to the insect. The transformed bacterium is then introduced to the insect.

The shuttle system provided in the present invention using natural microbes to deliver and express genes throughout insect colonies is a novel approach to insect management. Using target specific natural bacteria expressing target specific genes found in natural pathogens is an environmentally friendly alternative to traditional chemical control. This system will permanently eliminate pest insect colonies in a cost effective way that is a significant improvement over current baiting technology, because living cultures in baiting systems serve as a continuing source of inoculum, and are self-replicating, selfperpetuating and self-sustaining in the insect colony.

Microbial diversity associated with insects, such as the termite gut flora, provides raw material for genetic modification with a wide range of specificity and application. There is easy access to bacteria, such as the Enterobacteriaceae, that survive well under aerobic conditions and can be readily genetically modified. Because they occur in a variety of insect species (termites, ants, cockroaches, etc.), these bacteria represent a broad-spectrum shuttle system widely used in pest control. On the other hand, bacteria can also be relied on that have special growth requirements and are highly specific to a certain insect species. Such bacteria have a low chance of survival in the environment or potential for impact on any non-target species.

BRIEF DESCRIPTION OF THE DRAWINGS

FIG. 1 is a diagram of the pEGFP plasmid, an example of an expression vector that can be used in a "shuttle" bacterium in insects for the gene delivery and expression system of the present invention.

FIG. 2 shows the uptake of recombinant bacteria by workers of three colonies (3 columns) up 48 hours after workers were introduced to recombinant *Enterobacter* inoculated on filter paper. Error bars indicate standard deviation.

FIG. 3 shows the persistence over 12 weeks of recombinant bacteria in the gut of termites in three different colonies (3 columns), averaged over three replicates. Error bars indicate standard deviation.

FIG. 4 shows the transfer of recombinant bacteria between workers. Results for each of the three colonies were averaged over three replicates. Error bars indicate standard deviation.

FIG. 5 shows the transfer of recombinant bacteria between workers, tested every two hours for the first 12 hours and then at 26, 28, 32, 50, 56, and 76 hours for one colony, averaged over three replicates. Error bars indicate standard deviation.

FIG. 6 shows the uptake of recombinant bacteria in workers and soldiers and transfer from worker to soldier and vice versa averaged over three replicates for one colony. Error bars indicate standard deviation.

FIG. 7 shows the transfer of recombinant bacteria with reduced donor:recipient proportion averaged over three colonies and two replicates for each colony. Error bars indicate standard deviation.

DETAILED DESCRIPTION OF THE INVENTION

The present invention relates to a bacterium for the control of insects. The bacterium of the present invention is transformed with a nucleic acid construct that includes a nucleic acid molecule that encodes a protein or polypeptide that is toxic to insects. The nucleic aid encoding the toxin is operatively linked to transcriptional and translational control elements that allow for the expression of the toxin in the insect. The bacterium to be transformed is chosen from among those that are endogenous to (i.e., naturally occurring in) the insect to be controlled (i.e., the "target" insect). Particularly suitable as a host bacterium are organisms that naturally exist in the gut of the target insect.

The protein toxins discussed herein are typically referred to as "insecticides" in that the toxins are used as insect control agents. As used herein, to "control" insects means to inhibit, through a toxic effect, the ability of the pest insect to survive, grow, feed and/or reproduce, or to limit the insect-related damage attributable to the target insect population. "Insecticidal" as used herein is defined as a toxic biological activity capable of controlling insects. The nucleic acid encoding a protein or polypeptide that is toxic to the insect to be controlled may be derived from any of a variety of sources. Suitable insecticidal genes are of either prokaryotic or eukaryotic origin, and can be in their natural state or genetically modified. In addition to toxins acting directly against the insect, genes that produce toxins against microbial symbionts of the target species, such as certain bacteria or protozoa, can also be regarded as insecticidal. By killing the symbionts, the vital nutritional balance between host and symbiont, which is obligatory for the survival of the target species, can be disrupted. Regardless of their origin, any insecticidal genes can be inserted into the shuttle system of the present invention.

Toxicant producing genes suitable for the present invention can be obtained from entomopathogenic bacteria, such as *Bacillus thuringiensis* (Berliner), *Pseudomonas aeruginosa*, and *Serratia marcescens*, which cause considerable mortality in termites in laboratory experiments (U.S. patent application Ser. No. 20010026940A1 to Cardineau et al.; Smythe et al., "The Susceptibility of *Reticulitermes flavipes* (Kollar) and Other Termite Species to an Experimental Preparation of *Bacillus thuringiensis* Berliner," *J. Invertebrate Pathology* 7:423–426 (1965); Khan et al., "Pathogenicity of Locally Discovered *Bacillus thuringiensis* Strain to the Termites: *Heterotermes indicola* (Wassman) and *Microcerotermes championi* (Snyde)," *Pakistan J. of Sci. Res*. 29:12–13 (1977); Khan et al., "The Pathogenicity and Development of *Bacillus thuringiensis* in Termites," *Pakistan J. Zool*. 17:201–209 (1985); Khan et al., "The Pathogenicity of *Pseudomonas aeruginosa* Against Termites," *Pakistan J. Zool*. 24:243–245 (1992); Grace, J. K., "Biological Control Strategies for Suppression of Termites," *J. Agric. Entomol*. 14:281–289 (1997), which are hereby incorporated by reference in their entirety).

For example, there are several thousand *Bacillus thuringiensis* ("Bt") strains stored in genomic libraries and gene banks, producing the insecticidal Cry protein and/or Cyt crystal protein, which are active against a wide range of insects, including termites (Khetan, S. K., *Microbial Pest Control*, Marcel Dekker AG, New York (2001); Smythe et al., "The Susceptibility of *Reticulitermes flavipes* (Kollar) and Other Termite Species to an Experimental Preparation of *Bacillus thuringiensis* Berliner," *J. Invertebrate Pathology* 7:423426 (1965); Khan et al., "Pathogenicity of Locally Discovered *Bacillus thuringiensis* Strain to the Termites: *Heterotermes indicola* (Wassman) and *Microcerotermes championi* (Snyde)," *Pakistan J. of Sci. Res*. 29:12–13 (1977); Khan et al., "The Pathogenicity of *Pseudomonas aeruginosa* Against Termites," *Pakistan J. Zool*. 24:243–245 (1992), which are hereby incorporated by reference in their entirety).

Also suitable as toxin-encoding nucleic acids are those from any other *Bacillus* spp., such as the multitude of nucleotide sequences derived from B. *cereus*, B. *subtilis*, and other Bacillus species that are described in U.S. Pat. No. 5,889,174 to Warren et al., which is hereby incorporated by reference in its entirety. Other microbial nucleic acids suitable in the present invention encode toxins derived from *Photorhabdus*, including but not limited to, *Photorhabdus luminescens* (Bowen et al., "Insecticidal Toxins from Photorhabdus luminescens," *Science* 280:2129–2132 (1998); U.S. Pat. No. 6,282,413 to Kramer et al., and *Xenorhabdus* spp. (U.S. Pat. No. 6,048,838 to Ensign, which are hereby incorporated by reference in their entirety) which have been shown to be insecticidal and are presumed to have a comparatively broad range of applicability.

Genes encoding for fungal pesticides are also suitable for the present invention. An exemplary fungal toxin is the isolate from the fungus *Beauveria bassiana* (deposited in a public repository as isolate No. 447), which has been shown to have a high functional activity against fire ants (U.S. Pat. No. 4,925,663 to Stimac, which is hereby incorporated by reference in its entirety), cockroaches (WO 95/25430 to Stimac, which is hereby incorporated by reference in its entirety), and termites (U.S. patent application Ser. No. 20010006632 to Stimac et al., which is hereby incorporated by reference in its entirety), but has been used to date only in topical applications.

Some of the naturally occurring insecticidal genes that are suitable for the present invention, such as Bt toxins, are, or can be, readily genetically modified, using classical mutation or recombinant DNA techniques to increase efficiency and broaden the target range.

These insecticidal genes are usually encoded on a transmissible plasmid, and are well characterized. Sequence collections of most of these insecticidal genes are available in genomic libraries in the form of clones. In the alternative, a synthetic nucleic acid can be prepared chemically using a publicly available toxin-encoding nucleotide sequence. If not already available in the form of a natural plasmid or a plasmid construct, insecticidal genes, regardless of source (i.e., prokaryotic, eukaryotic, plasmid or chromosomal origin) can be cloned into an expression vector and cultured using host bacteria such as *Bacillus, Clostridium*, etc., and used in the present invention.

Another source of nucleic acid suitable in the present invention is genes encoded in higher organisms. For example, research with arachnid venoms has identified and partially characterized a number of peptide toxins with insecticidal properties (Krapcho et al., "Characterization and Cloning of Insecticidal Peptides from the Primitive Weaving Spider *Diguetia canities,*" *Ins. Biochem. Molec. Biol.* 25:991–1000 (1995); Quistad et al., "Isolation and Sequencing of Insecticidal Peptides from the Primitive Hunting Spider, *Plectreurys tristis* (Simon)," *J. Biol. Chem.* 269:11098–11101 (1994), Jackson et al., "Spider Toxins: Recent Applications in Neurobiology," *Ann. Rev. Neurosci.*, 12:405 (1989); U.S. Pat. No. 5,741,669 to Krapcho et al.; which are hereby incorporated by reference in their entirety). Multiple peptide toxins that antagonize synaptic transmission in insects have been isolated from the spider *Agelenopsis aperta* (Adams et al., "Isolation and Biological Activity of Synaptic Toxins from the Venom of The Funnel Web Spider, Agelenopsis aperta", in *Insect Neurochemistry and Neuro-Physiology*, Borkevec and Gelman, eds., Humana Press, New Jersey (1986); which is hereby incorporated by reference in its entirety). Venom of the Joro spider, *Nephila clavata*, has been disclosed as containing a toxin that shows glutamate receptor inhibitory activity in an insect electrophysiologic assay, suggesting its use as an insecticide for the disruption of biosynthetic pathways in the target insect (U.S. Pat. No. 4,855,405 to Yoshioka et al.; which is hereby incorporated by reference in its entirety).

Nucleic acids encoding scorpion toxins are also suitable in the present invention (Carbonell et al., "Synthesis of a Gene Coding For an Insect-Specific Scorpion Neurotoxin And Attempts To Express It Using Baculovirus Vectors", *Gene* 73:409–418 (1988), which is hereby incorporated by reference in its entirety). The nucleic acids encoding these toxins and others functionally similar are suitable for use in the present invention.

Those skilled in the art will appreciate that the nucleic acid molecules encoding toxins for use in the present invention may be isolated from the source organism, or chemically or synthetically prepared using the known nucleic acid sequence. As used herein, the term "nucleic acid" refers to polynucleotides such as DNA, and where appropriate, RNA. The term should also be understood to include, as equivalents, analogs of either RNA or DNA made from nucleotide analogs.

Also suitable for the present invention are toxin-encoding nucleic acids of the present invention that are altered in various ways, including amino acid substitutions, deletions, truncations, and insertions. Methods for such manipulations are generally known in the art. For example, amino acid sequence variants of the insecticidal proteins or polypeptides can be prepared by mutations in the DNA, provided such variants still possess the desired insecticidal activity. Obviously, any mutations made in the nucleic acid encoding the variant toxin must not place the sequence out of reading frame and preferably will not create complementary regions that could produce secondary mRNA structure.

Most deletions, insertions, and substitutions of the protein sequence are not expected to produce radical changes in the characteristics of the toxic protein or polypeptide. However, when it is difficult to predict the exact effect of the substitution, deletion, or insertion in advance of doing so, one skilled in the art will appreciate that the effect can be readily evaluated by routine screening assays.

The toxin-encoding nucleic acids construct of the present invention can then be introduced into an appropriate bacterial host cell of the present invention under conditions that allow for stable maintenance and expression of the gene by any number of methods known to those skilled in the art, or as described by Ausubel et al., "Short Protocols in Molecular Biology, " New York:Wiley (1999), and Sambrook et al., *Molecular Cloning: A Laboratory Manual*, Cold Springs Laboratory, Cold Springs Harbor, New York (1989), which are hereby incorporated by reference in their entirety.

Generally, this involves inserting the nucleic acid molecule into an expression system to which the molecule is heterologous (i.e., not normally present). The heterologous nucleic acid molecule is inserted into the expression system, vector, or bacterial chromosome in the proper sense (5'→3') orientation and correct reading frame, creating a nucleic acid construct that can be expressed in the target insect. Such a construct is also provided with transcriptional and translational regulatory signals for the expression of the toxin gene in the host. "Regulatory elements" refers to sequences involved in controlling the expression of a nucleotide sequence. Regulatory elements comprise a promoter operably linked to the nucleotide sequence of interest, and termination signals. They also typically encompass sequences required for proper translation of the nucleotide sequence. Depending upon the host-vector system utilized, any one of a number of suitable transcription and translation elements can be used.

Transcription of DNA is dependent upon the presence of a promoter which is a DNA sequence that directs the binding of RNA polymerase and thereby promotes mRNA synthesis. The DNA sequences of eukaryotic promoters differ from those of procaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper procaryotic signals which differ from those of eukaryotes. Efficient translation of mRNA in prokaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength"(i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *Enterobacteriaceae*, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgamo (SD) sequence about 7–9 bases 5'to the initiation codon (ATG) to provide a ribosome binding site. Thus, any SD-ATG combination that can be utilized by host cell ribosomes may be employed. Additionally, any SD-ATG combination produced by recombinant DNA or other techniques involving incorporation of synthetic nucleotides may be used.

The introduction of a gene into a host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The nucleic acid molecules of the present invention may be inserted into any of the many available expression vectors and cell systems using reagents that are well known in the art.

Suitable plasmids for preparation of the nucleic acid construct of the present invention include, for example, pEGFP, shown in FIG. 1, and prepared as described in Example 1, below, as well as any others known to be compatible with the bacterial host system as described herein. This includes, but is not limited to, the following vectors: lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F.W. Studier et. al., "Use of T7 RNA Polymerase to Direct Expression of Cloned Genes," *Gene Expression Technology* Vol. 185 (1990), which is hereby incorporated by reference in its entirety), and any derivatives thereof.

The toxin-encoding nucleic acid sequences are cloned into the vector of choice using standard cloning procedures in the art, such as described in Sambrook et al., *Molecular Cloning: A Laboratorv Manual*, Cold Springs Laboratory, Cold Springs Harbor, New York (1989) and U.S. Pat. No. 4,237,224 to Cohen and Boyer, which are hereby incorporated by reference in their entirety.

The nucleic acid molecules of the present invention can be optimized for enhanced expression in insects, such that when the recombinant bacteria of the present invention are ingested by pest insect, the toxin gene is expressed in the gut of the target insect. Therefore, particularly suitable as host cells are the naturally occurring bacteria of the gut of the target insect. By using genetically modified, naturally occurring gut bacteria of target insects as a "shuttle" for spreading the toxic gene(s), the efficacy of the toxin is enhanced. Because they are naturally associated with the target species, these shuttle bacteria are non-repellent and are easily introduced into the target insect through ingestion.

Exemplary bacteria for use as shuttle host cells include any of the bacteria which occur naturally in a target insect, including, but not limited to, those characterized as follows: Proteobacter, including the genus *Pseudomonas*; Actinobacter, including Priopionibacterium and Corynebacterium; Firmicutes, including the any species of the genera *Mycoplasma, Bacillus, Streptococcus, Staphylococcus*; Fibrobacteres; Spirochaetes, including *Treponoma* and *Borrelia*; Bacteroides, including the genera *Bacteroides* and *Flavobacterium*; and "Termite Group I". Also suitable are any bacteria of the Enterobacteriaceae, including the genus Serratia, including, but not limited to *S. marcescens, S. entomophila, S. proteamaculans*; any species of *Enterobacter*, including, but not limited to, *E. cloacae, E. aerogenes, E. dissolvens, E. agglomerans, E. hafniae*; and any species belonging to the following genera: *Citrobacter, Escherichia, Klebsiella, Kluyvera, Panotea, Proteus, Salmonella, Xenorhabdus* and *Yokenella.*

Hosts or pathogens that are not derived from the target organism often have repellent effects and are subsequently avoided. Social behavior, such as grooming, combats effectively any infection, as does recognition and isolation of infected individuals and the immune defense of insects.

Furthermore, pathogens in their native state often have only a weak potency. Recognition on the level of the individual as well as on the level of the immune system can be avoided by using natural microbes as "Trojan Horses," carrying and expressing the pathogenic genes.

In addition to the above-mentioned advantage of genetically modifying bacteria normally associated with the target species as shuttles for recombinant genes, molecular genetic techniques allow customization of the product. For example, rate and amount of the gene product, and thus the speed of action, can be regulated by the choice of promoters and enhancers. Field-life can be increased or suicide factors can be introduced to limit the life of the shuttle to minimize any environmental impact. Multiple genes can be cloned into the shuttle to avoid resistance and enhance effect on the target organism.

The present invention also relates to a method for insect control. This method involves isolating a bacterium that is endogenous to the insect to be controlled, and genetically modifying the bacterium by transforming the bacterium with a plasmid containing a nucleic acid molecule encoding a protein or polypeptide which, when expressed in the insect, is toxic to the insect. The transformed bacterium is then introduced to the environment of the pest insect to be controlled.

The isolation of bacterium endogenous to the target insect is carried out using techniques known to those in the art or as described in Example 1, below. "Genetically modifying" as used herein refers to the transformation of a bacterium native to the insect with a nucleic acid encoding a protein or polypeptide that is toxic to the insect when expressed in the insect from any of a variety of sources. Suitable for this aspect of the present invention are expression vectors, including, but not limited to plasmids and viral vectors; bacterial hosts; and nucleic acids that encode insecticidal toxins such as taught above and in the Examples, below. Suitable for the preparation of such genetically modified bacterium are any methods of transfection and transformation taught herein or known to those in the art, such as described in Sambrook et al., *Molecular Cloning: A Laboratory Manual*, Cold Springs Laboratory, Cold Springs Harbor, New York (1989); U.S. Pat. No. 4,237,224 to Cohen and Boyer; and Ausubel et al., *Short Protocols in Molecular Biology*, Wiley, New York (1999), which are hereby incorporated by reference in their entirety.

Once a bacterium is transformed in accordance with the present invention, it can further treated, or combined with other materials to be suitable as an insect food source, or an additive thereto. Alternatively, the modified bacterium containing toxic genes can be directly applied to the habitat and environs of the pest population. Once the toxin-encoding bacterium is present in the pest habitat, the foragers of the population will provide a means of transmission throughout the colony via food exchange and grooming among nestmates. Because the bacterial hosts are endogenous to the insects infected with the toxin gene, they are not recognized as "foreign" by the immune system of the target, and are not rejected or eliminated by an immune response. Thus, the toxin-encoding bacterium proliferate in the target insect. Persistence in the foragers allows for the spread of the bacterium through the colony, even to the difficult-to-reach reproductives of the population. With the demise of the reproductive members, the pest population is effectively terminated.

Potential targets for pest control using bacterial shuttle systems are mainly, but not exclusively, insect species which harbor and transfer microbes by social interactions, such as termites, roaches, and certain ant species.

The present invention also relates to a method of delivering and expressing a gene in an insect. This method involves isolating a bacterium endogenous to the insect, and transforming that bacterium with a nucleic acid molecule encoding a protein or polypeptide exogenous (i.e., foreign) to the insect. The transformed bacterium is then introduced to the insect. This method can be carried out using the reagents and methods described above, and in the Examples, below.

EXAMPLES

Example 1

Isolation of Gut Bacteria and Preparation of Recombinant Bacteria

Bacteria were isolated from termite intestinal track ("guts") and modified genetically to act as self-replicating and self-sustaining shuttles for delivering and expressing genes throughout a termite colony.

The Formosan subterranean termite (*Coptotermes formosanus* Shiraki) was used as a model species, because improved management of this important pest species is sorely needed. Workers and soldiers were collected from three colonies on the University of Hawaii campus.

Termites were anesthetized by an ice bath, the mouth and anus were sealed with paraffin, and the surface was sterilized with 80% alcohol. Guts were extracted, streaked on a wide selection of media, and cultured under aerobic and anaerobic conditions to assure the recovery of a wide array of gut microbes. Isolated strains have been described using standard morphological and biochemical techniques and 16S rDNA sequencing.

Marker genes were introduced into isolated bacteria using plasmid mediated transformation with standard protocols (Ausubel et al., "Short Protocols in Molecular Biology," New York: Wiley (1999), which is hereby incorporated by reference in its entirety). The plasmid pEGFP, (Clontech, Palo Alto, Calif.) carries the ampicillin resistance gene ("amp") as a genetic marker for selective culture, as well as the Green Fluorescent Protein gene ("GFP") that allows easy screening. See FIG. 1. Transformed bacteria are identified by expressing GFP, a visual marker that glows green when excited with UV light.

Genetically modified *Enterobacter* were cultured in Brain Heart Infusion ("BHI") media (Difco/Becton Dickinson, Sparks, MD) with ampicillin (10 $\mu$l/ml), and overnight incubation at 25–30° C. The numbers of colony forming units (CFU) was determined by dilution series on LB agar containing ampicillin (10 $\mu$g/ml) and screening for GFP expression. Overnight cultures contain between $10^8$ and $10^9$ CFU per ml.

BHI+amp media was inoculated with recombinant *Enterobacter* and grown overnight at 25–30° C. The overnight culture was then diluted (1:2) with distilled water, and 500 $\mu$p (containing approximately $3\times10^8$ CFU) applied to a Whatrnan filter paper circle placed in a 100×15 mm petri dish. The termites were placed in the dish and allowed to feed on the paper, ingesting the recombinant bacteria. Negative controls were fed filter paper treated with distilled water only (500 $\mu$l). Termites were checked for presence of recombinant bacteria by removing their whole guts aseptically and crushing the guts in sterile BHI+amp media. The culture was grown overnight under selective conditions. The presence/ absence of recombinant bacteria in the overnight culture was evaluated using UV light (254–365 nm), and confirmed by streaking of the culture on LB+amp agar plates. All termites were maintained in petri dishes at room temperature, and, every day, dead individuals were removed, petri dishes cleaned out to avoid re-inoculation through feces, and filter paper was changed and replenished with fresh water.

For testing transfer of recombinant bacteria, donor termites were prepared by feeding them with recombinant *Enterobacter* twice a day for two days, and subsets of these were tested to ensure that donors contained GFP. Donors were combined with recipients that were maintained under the same conditions as the donors, but were fed with water on filter paper only. Guts were pulled from recipients to test for the presence of recombinant bacteria. To distinguish between donors and recipients, one or the other category were dyed. Sudan Fat Red (Sigma-Aldrich, Milwaukee, Wis.) dyed paper was prepared (6.0 mg stain/paper) and placed in glass petri dishes. Termites were allowed to feed for 7–10 days, after which they obtained a red coloration, distinct from the natural wild-type white color. Dye has no influence on uptake, transfer, and stability of recombinant bacteria in termites. To date, over 15 strains of bacteria have been isolated, ranging from easy to culture and ubiquitous Enterobacteriaceae species to strains novel to science and highly specific to termites. Several different genera of the Enterobacteriaceae (e.g., *Citrobacter, Klebsiella* and *Enterobacter* spp.) have been successfully transformed with the plasmid containing the genetic markers (amp resistance, GFP). The recombinant bacteria show stable gene expression over time. In behavioral and consumption tests, there is no repellency effect of filter paper inoculated with recombinant bacteria. Termites walk over inoculated filter paper and consume bacteria as regular part of their diet.

*Enterobacter cloacae*, a strain found in ample amounts in the termite gut, was chosen as one model shuttle bacterium to deliver and express genes throughout a termite colony. Recombinant *Enterobacter* were fed to termites in a series of experiment. The rate of uptake, persistence, and transfer of recombinant bacteria among termites were measured.

Example 2

Uptake of Recombinant Bacteria by Workers Feeding on Inoculated Filter Paper

Figure 2:
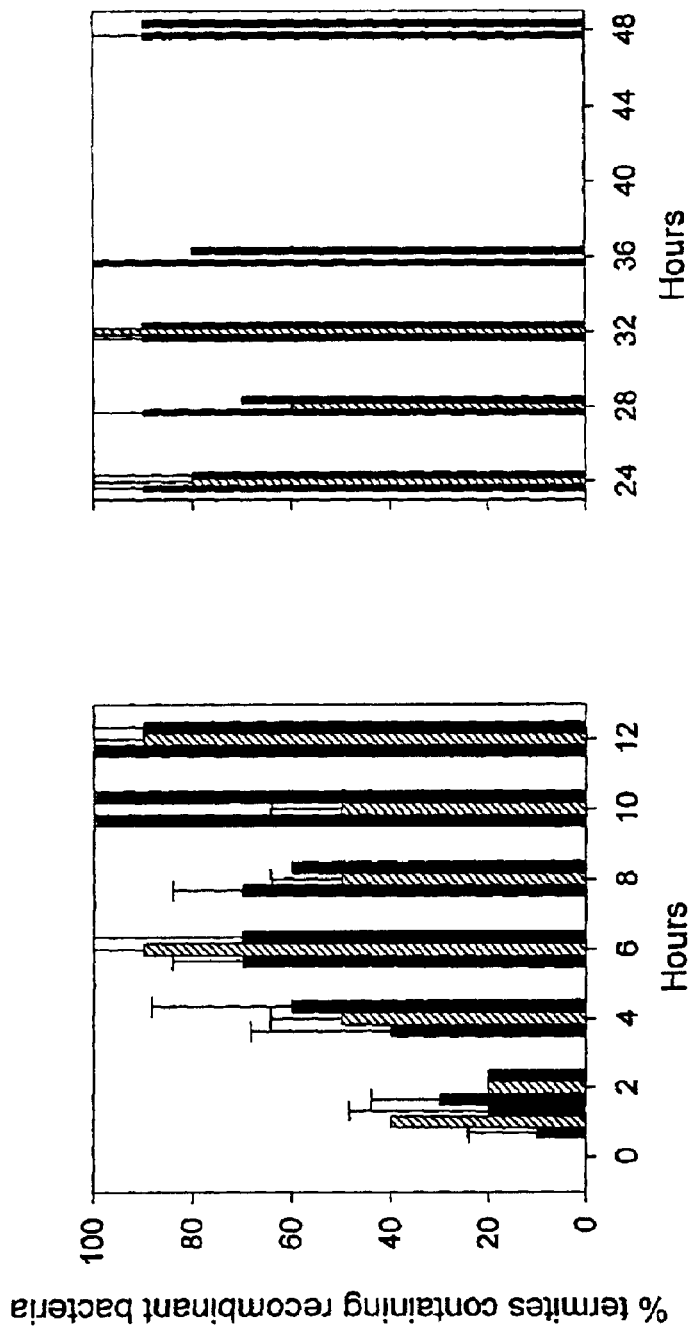

Workers from three colonies were fed with recombinant *Enterobacter* inoculated on filter paper in two replicates (dyed and non-dyed). 10 individuals were tested for harboring recombinant bacteria in their gut every two hours after initial exposure for 12 hours, and then after 24, 28, 32, 36, and 48 hours. Results are shown in FIG. 2. At each time point, the per cent of termites containing recombinant bacteria from each of the three colonies is shown. No difference was seen in the rate of uptake was found between dyed and non-dyed workers. On average, recombinant bacteria were present in 85 to 100% of the workers after only 12 hours of feeding. The results show rapid uptake of recombinant bacteria by termite workers through direct feeding.

Example 3

Long-Term Persistence of Recombinant Bacteria in the Termite Gut

The persistence of recombinant bacteria in the gut of the termites was evaluated from samples of three different colonies. The results were averaged over three replicates for each colony. Workers were fed with recombinant bacteria for two days, after which they were transferred to new dishes and fed with water only. Petri dishes were cleaned out each day to avoid re-inoculation with bacteria through feces. Guts from up to 20 termites were taken once a week to test for the presence of recombinant bacteria.

Figure 3:
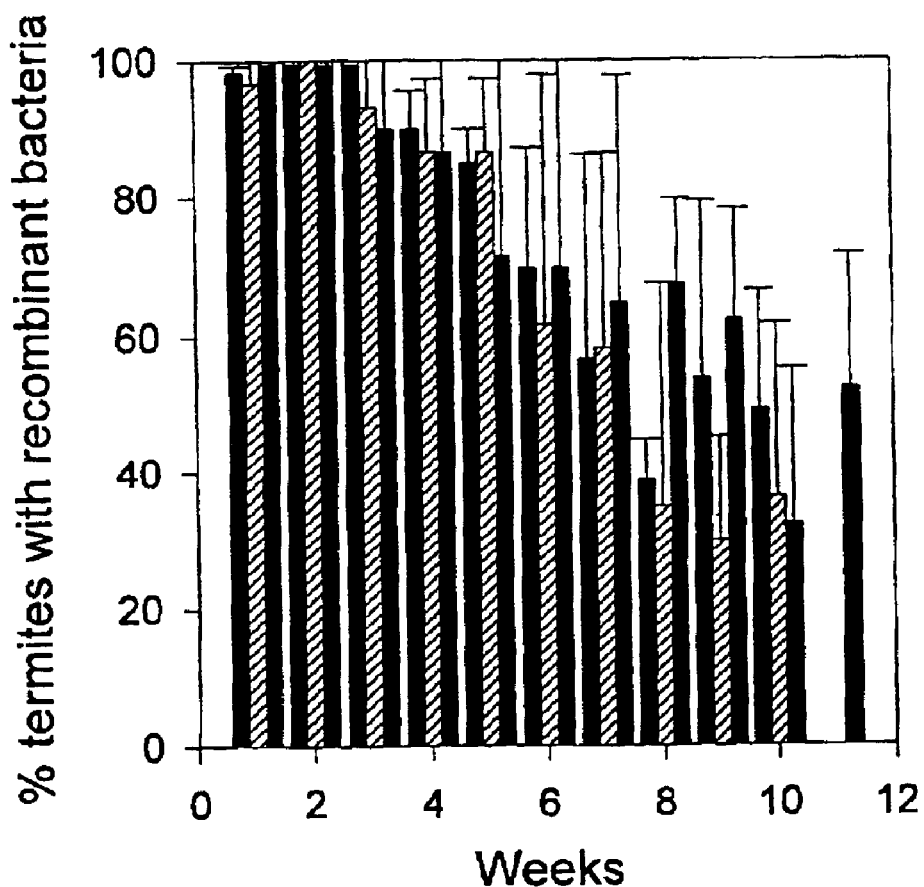

As shown in FIG. 3, the recombinant bacteria established a stable, self-replicating, and self-perpetuating population in the termite gut that needed no augmentation for up to several weeks. In this study, recombinant bacteria continued to persist as long as the termites were healthy. After 8 weeks, the termite population declined rapidly, which contributed to the loss of recombinant bacteria.

Example 4

Transfer of Recombinant Bacteria from Worker to Worker

Figure 4:
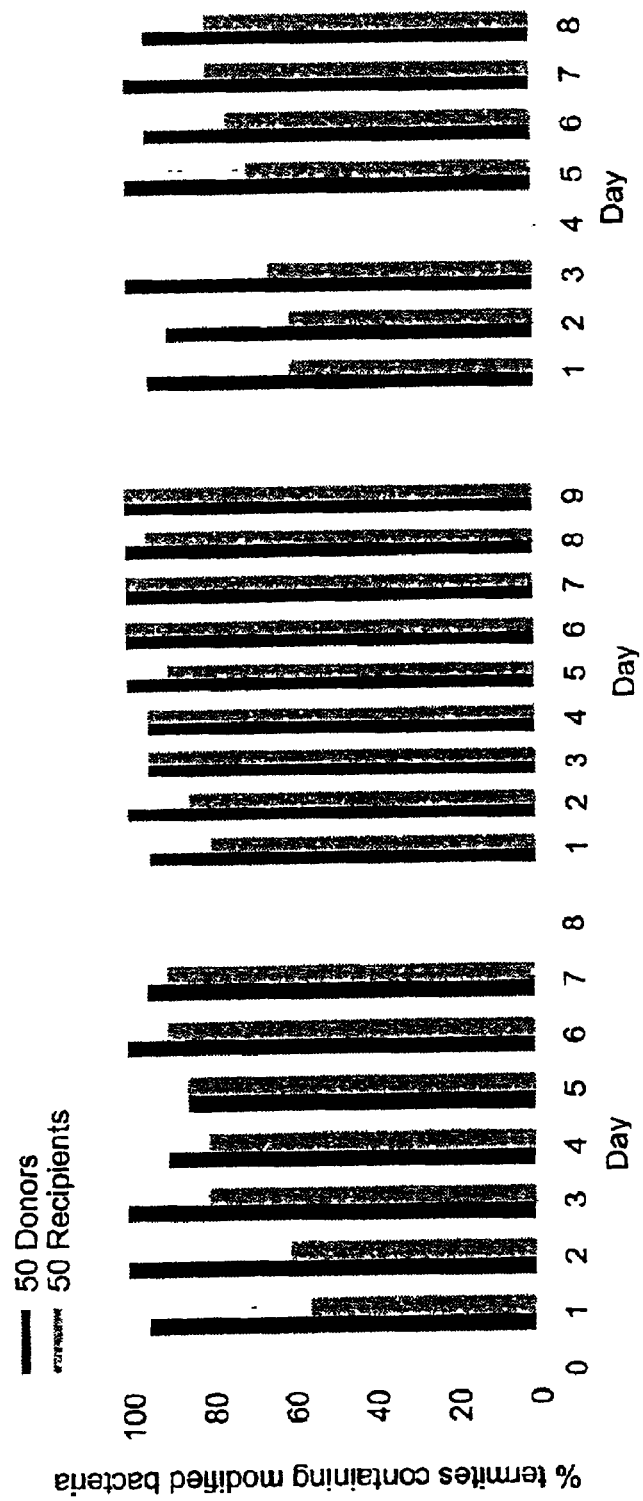

This experiment was conducted for three different colonies with three replicates for each colony and an equal donor to recipient ratio. The rate of transfer of recombinant bacteria among termites was tested (a) daily for up to 9 days and (b) every two hours for the first 12 hours and then after at 26, 28, 32, 50, 56, and 76 hours. Each experiment was repeated thrice for each of the three colonies. Donors (i.e., workers fed with recombinant bacteria) and recipients (fed with water only) could be recognized by dyeing one category. Fifty donors were combined with 50 recipients in a petri dish. Each following day, guts were pulled from an aliquot of five donors and five recipients and screened for the presence of recombinant bacteria. FIG. 4 shows that after only one day of combining donors and recipients, 55–80% of the recipients received recombinant bacteria. The proportions of recipients containing recombinant bacteria increased over time and reached 80–100% after a week for each of the three colonies.

Figure 5:
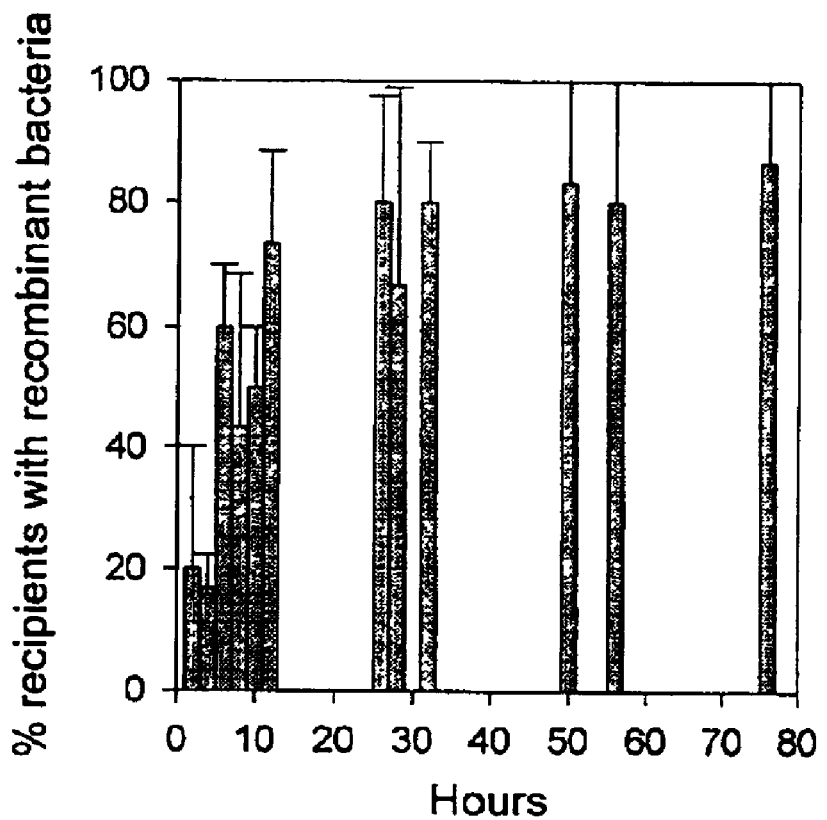

Because most of the transfer occurred within the first 12 hours, an additional experiment was conducted to measure the initial transfer rate on a finer scale, i.e., every two hours for the first 12 hours, and then at 26, 28, 32, 50, 56, and 76 hours. As shown in FIG. 5, a steep increase of the percentage of recipients containing recombinant bacteria occurred in the first 12 hours after initial combination (to over 70%). This suggests a rapid multiplication effect by recipients becoming secondary donors.

Example 5

Transfer of Recombinant Bacteria Between Workers and Soldiers

Figure 6:
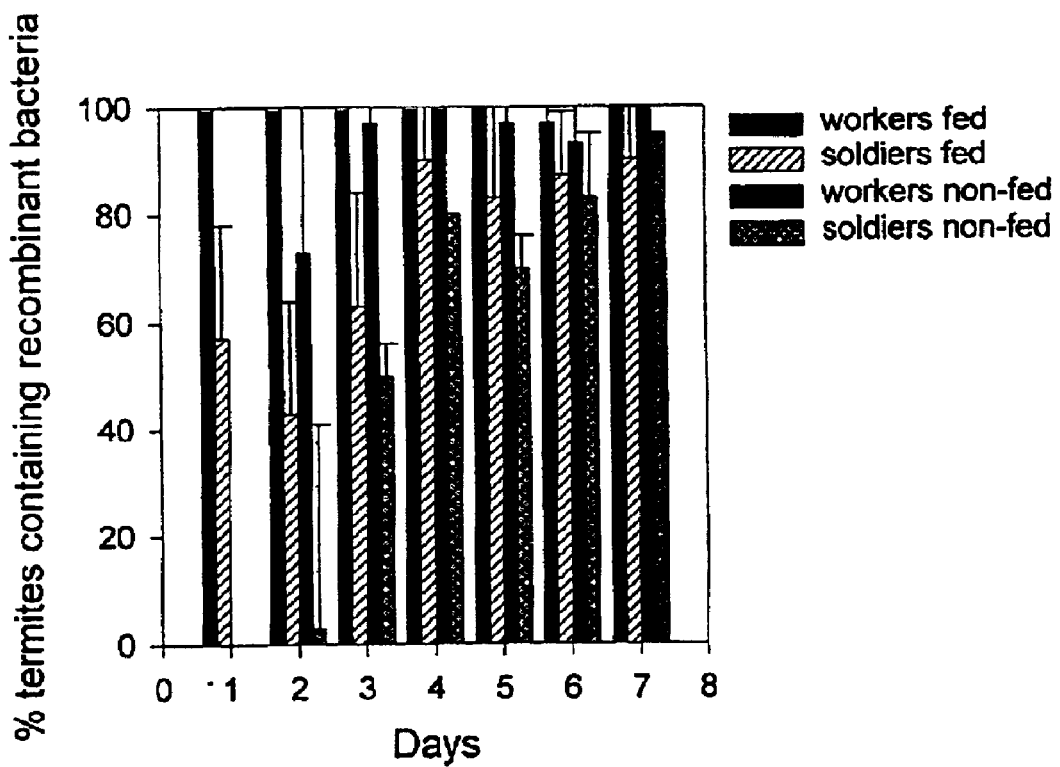

Worker-donors (i.e., workers fed with recombinant bacteria) were combined with soldier-recipients (fed with water only), and soldier-donors with worker-recipients for the three colonies. Each day over the course of a week, 10 guts were pulled from each category and checked for the presence of recombinant bacteria. As shown in FIG. 6, recombinant bacteria were transferred from workers to soldiers in as little as 24 hours (23% on average), increasing over time (80% after 4 days, and 95% after one week). It was also demonstrated that, when placed on filter paper inoculated with recombinant bacteria, soldier termites were able to take up the bacteria without the help of workers (47% on average, after 48 hours). After 24 hours of exposure to these fed soldiers, previously non-fed workers showed the presence of recombinant bacteria in 73%, increasing to 97% after 72 hours. The sharp increase was probably helped by subsequent worker-toworker spread after initial infection by fed soldiers.

Generally, soldiers are believed not to be able to feed on their own. However, they still take up recombinant bacteria from the substrate as well as from nestmate workers and are able to pass bacteria to non-fed workers. Although soldier uptake and transfer is not as efficient as worker uptake and transfer, it adds to the overall efficiency of the shuttle system.

Example 6

Transfer Using a Reduced Proportion of Donors

Figure 7:
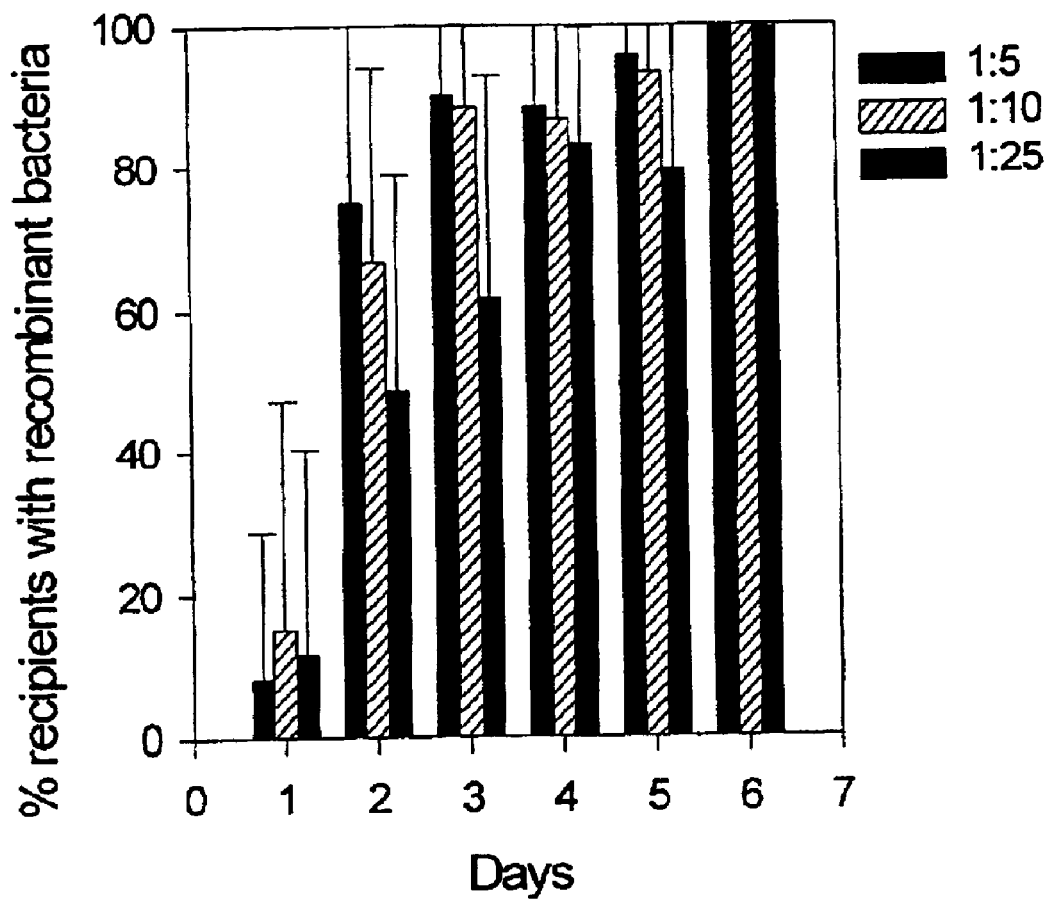

For application in termite control, the shuttle system of the present invention has to transfer efficiently even if only a few individuals can be inoculated as donors. Therefore, using the same experimental design as described in Example 4, the donor:recipient ratio was varied from 1:5 to 1:25. For each colony, the experiment was repeated twice, with both non-dyed and dyed termites acting as donors, and non-dyed and dyed termites acting as recipients. As shown in FIG. 7, there was little difference in the rate of transfer at each of the different ratios. Therefore, only a few donors are required to spread recombinant bacteria throughout the colony. This is probably due to the self-replicating multiplication effect of recipients becoming secondary donors. This is key to fast spread of bacteria to a high number of individuals.

Using microbes isolated from the target species and genetically modified to express marker genes provides an efficient system for delivering and expressing genes throughout a social insect colony. The present invention teaches that recombinant bacteria are rapidly introduced into termites by ingestion and establish a stable self-replicating and self-perpetuating population for at least several weeks. Transfer among termites occurs rapidly and requires only a few inoculated donors. Such shuttle systems using microbes naturally associated with the target species provide the means to spread genes producing insecticidal toxins efficiently throughout social and subsocial insect colonies.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for delivering and expressing an exogenous gene in a colonial or social insect population comprising:

isolating a bacterium endogenous to the colonial or social insect population;

transforming said bacterium with a nucleic acid molecule encoding a protein or polypeptide that is exogenous to the colonial or social insect population, wherein the exogenous gene is detrimental to survival of the colonial or social insect population; and introducing said transformed bacterium live into a food source of the colonial or social insect population.

2. The method according to claim 1, wherein the nucleic acid molecule is in a construct further comprising transcriptional and translational elements operably linked to the nucleic acid molecule to allow expression of the nucleic acid molecule in the insect.

3. The method according to claim 1, wherein the bacterium is isolated from the gut of the insect.

4. The method according to claim 3, wherein the bacterium is selected from the group consisting of Proteobacter, Actinobacteria, Fibrobacteres; Spirochaetes, Firmicutes, Bacteroides, Enterobacteriaceae, and Termite Group I.

5. The method according to claim 4, wherein the bacterium is an Enterobacteriaceae.

6. The method according to claim 5, wherein the bacterium is selected from the group consisting of *Enterobacter* spp., *Citrobacter* spp., *Klebsiella* spp., *Serratia* spp., *Kluyvera* spp., *Pantoea* spp., *Proteus* spp., *Salmonella* spp., *Xenorhabdus* spp., and *Yokenella* spp.

7. The method according to claim 6, wherein the bacterium is selected from the group consisting of *Enterobacter cloacae, Enterobacter aerogenes, Enterobacter dissolvens, Enterobacter agglomerans*, and *Enterobacter hafniae.*

8. The method according to claim 6, wherein the bacterium is selected from the group consisting of *Serratia marcescens, Serratia entomophila*, and *Serratia proteamaculans.*

9. The method according to claim 4, wherein the bacterium is a Proteobacter.

10. The method according to claim 9, wherein the bacterium is a *Pseudomonas* spp.

11. The method according to claim 4, wherein the bacterium is a Firmicutes.

12. The method according to claim 11, wherein the bacterium is selected from the group consisting of *Mycoplasma* spp., *Bacillus* spp., *Streptococcus* spp., and *Staphylococcus* spp.

13. The method according to claim 12, wherein the bacterium is selected from the group consisting of *Bacillus thuringiensis, Bacillus cereus*, and *Bacillus subtilis.*

14. The method according to claim 1, wherein the insect is selected from the group consisting of a termite, an ant, and a cockroach.

15. The method according to claim 14, wherein the insect is a termite.

16. The method according to claim 7, wherein the bacterium is *Enterobacteriaceae cloacae.*

* * * * *